United States Patent
Ulin (10) Patent No.: US 7,285,423 B2
(45) Date of Patent: Oct. 23, 2007

(54) PENETRABLE PRESSURE PROOF SEALING FOR A CONTAINER

(75) Inventor: Johan Urban Ingemar Ulin, Uppsala (SE)

(73) Assignee: Biotage AB, Uppsala (SE)

( * ) Notice: Subject to any disclaimer, the term of this patent is extended or adjusted under 35 U.S.C. 154(b) by 528 days.

(21) Appl. No.: 10/025,220

(22) Filed: Dec. 19, 2001

(65) Prior Publication Data

US 2002/0090736 A1 Jul. 11, 2002

Related U.S. Application Data

(60) Provisional application No. 60/257,091, filed on Dec. 22, 2000.

(51) Int. Cl.
*G01N 1/10* (2006.01)

(52) U.S. Cl. .............. 436/180; 422/99; 422/100; 422/101; 73/1.73; 92/15

(58) Field of Classification Search .......... 422/99–104; 436/180; 73/1.73; 92/15
See application file for complete search history.

(56) References Cited

U.S. PATENT DOCUMENTS

| | | | |
|---|---|---|---|
| 3,693,455 A | 9/1972 | Harding et al. | |
| 3,991,912 A | 11/1976 | Soto | |
| 4,952,498 A * | 8/1990 | Waters | 435/34 |
| 5,270,010 A * | 12/1993 | Lautenschlager | 422/102 |
| 5,345,066 A | 9/1994 | Knapp et al. | |
| 5,382,414 A * | 1/1995 | Lautenschlager | 422/186 |
| 5,471,022 A * | 11/1995 | Kiss et al. | 200/83 B |
| 5,637,803 A | 6/1997 | Schalk et al. | |
| 5,981,924 A | 11/1999 | Lautenschlager | |
| 6,001,087 A * | 12/1999 | Zurcher | 604/411 |
| 6,045,755 A | 4/2000 | Lebl et al. | |
| 6,114,680 A | 9/2000 | Bauk et al. | |

FOREIGN PATENT DOCUMENTS

| | | |
|---|---|---|
| EP | 0 476 386 A | 3/1992 |
| FR | 2 674 146 A | 9/1992 |
| GB | 2 121 016 A | 12/1983 |
| WO | WO 99 54034 A | 10/1999 |

OTHER PUBLICATIONS

European Patent Office Communication Pursuant to Article 96(2) and Rule 51(4) EPC (dated May 3, 2006) in counterpart European Patent Application No. 01 272 432.4-1234.

(Continued)

*Primary Examiner*—Jill Warden
*Assistant Examiner*—Jyoti Nagpaul
(74) *Attorney, Agent, or Firm*—Harness, Dickey & Pierce, P.L.C.

(57) ABSTRACT

A seal mechanism, apparatus and method are suggested for confining a chemical reaction in a reaction vessel that is accessible through a self-sealing diaphragm. A movable plunger is reversibly operable between a retracted position where the diaphragm is accessible for injection and/or extraction of reagents, and an operational position wherein the plunger is controlled to apply an external pressure in direct contact with the self-sealing diaphragm.

13 Claims, 4 Drawing Sheets

OTHER PUBLICATIONS

European Patent Office Communication Pursuant to Article 96(2) EPC (dated Feb. 14, 2005) in counterpart European Patent Application No. 01 272 432.4-1234.
PCT International Search Report (dated Jul. 19, 2002) in counterpart PCT Application No. PCT/SE01/02876.
PCT Written Opinion, (Sep. 13, 2002) in counterpart PCT Application No. PCT/SE01/02876.
PCT International Preliminary Examination Report (dated Mar. 17, 2003) in counterpart PCT Application No. PCT/SE01/02876.

* cited by examiner

PENETRABLE PRESSURE PROOF SEALING FOR A CONTAINER

This application claims priority on U.S. Provisional application No. 60/257,091 filed on Dec. 22, 2000 under 35 U.S.C. § 119(e), the entire contents of which are hereby incorporated herein by reference in its entirety and for all purposes.

TECHNICAL FIELD

The invention relates to a penetrable pressure proof sealing for a container so as to enable injection and/or extraction of substance to/from the container, in particular, reaction vessels. More specifically, the invention relates to a seal mechanism, apparatus and method for confining a chemical reaction in a reaction vessel that is accessible through a self-sealing diaphragm.

BACKGROUND AND PRIOR ART

When performing a chemical reaction in a vial or test tube that is sealed with a lid covering an opening of the container, said lid being penetrated so as to inject e.g. a reagent or solvent to the content of the container. In order to initiate or to accelerate the chemical reaction, the content is often heated, for example by exposing the content to microwave energy, whereby an increase of pressure typically is generated in the container. Thus, a condensation or evaporation of the content in the container will take place, if the penetration through the lid is not closed. Conventionally, the lid may be exchanged for a new non-penetrated lid each time that the lid has been penetrated. Alternatively, the lid may be a screw cap that can be removed each time an injection or extraction is carried out. These solutions are time consuming and complicated for the operator.

Prior art references disclose differently structured seals for containers.

EP 0 476 386 describes a port assembly for an enteric feeding bag, wherein the bag prevents the insertion of a spike of a parental set, while permitting insertion of a spike of an enteric set into an enteric container.

U.S. Pat. No. 3,991,912 describe an apparatus for dispensing medicaments or the like, and in particular a sealed package/container for a liquid medicament and a separate attachable dispenser for use therewith. When the inset conduit of the dispenser has penetrated the container, the gravity acting on the content in the container will cause the double-folded walls in the bottom portion of the container to wrap around said inset conduit and thus prevent seepage through the penetrated portion.

GB 2,121,016 describes an evacuation device for a container, and which is provided with a self-sealing diaphragm. The sealing diaphragm is arranged to bend inwardly into the enlarged space when pressure is applied thereto by a connection device penetrating it. Subsequently, the seal self-seals due to its elasticity when the connection device is removed. Thus, fluid may be removed from the container more than once.

U.S. Pat. No. 6,045,755 disclose a reaction vessel having a penetrable septum. A compressible collar on the external side of the septum provides an orifice for inserting a needle through the septum. The orifice becomes occluded and seals the vessel when the collar is vertically compressed by means of a screw cap in threaded engagement with the vessel. (See FIGS. 12A and 12B).

U.S. Pat. No. 3,693,455 disclose a reaction vessel with a double septum injection port. The two septas are vertically compressed between steel discs when a locking nut is tightened in threaded engagement with the vessel.

In the course of designing cost effective chemical processes, there is an urgent demand for a new solution to the problem of confining a chemical reaction in a vessel that provides repeated access to its inner volume. A solution to this problem preferably involves the possibility of performing automated chemical processes.

SUMMARY OF INVENTION

It is an object of the present invention to provide a penetrable pressure proof sealing for a reaction vessel, said sealing making it possible to inject or extract substance to/from the reaction vessel a plurality of times, and wherein the reaction vessel can be set under pressure between the injections/extractions due to the pressure proof sealing.

Another object of the invention is to provide a seal mechanism, apparatus and method for confining a chemical reaction in a reaction vessel that is accessible through a self-sealing diaphragm.

It is further an object to provide a sealing that is easy to use and to implement.

These and other objects are met in a seal mechanism as defined in the accompanying claim 1, an apparatus as defined by claim 8, and a method as defined by claim 15. Advantageous embodiments of the invention are further defined in the subordinated claims.

Briefly, the invention suggests a seal mechanism for confining a chemical reaction in a reaction vessel (1) that is accessible through a penetrable, self-sealing diaphragm (5) covering an opening (4) of the reaction vessel through which reagents are injected and/or extracted. Said seal mechanism comprises a movable plunger (7) that is reversibly operable into abutting contact with an external side of the diaphragm wherein the plunger is effective for preventing an outward deflection of the diaphragm caused by an increase of internal pressure, resulting from the chemical reaction and/or from heating the contents in the vessel.

The invention also suggests an apparatus for performing chemical reactions wherein one or more reaction vessels (1) are supported and successively moved in parallel or in series to a position for microwave energy exposure, each reaction vessel having a penetrable, self-sealing diaphragm (5) covering an opening (4) of the reaction vessel. The apparatus has dispensing means capable of penetrating the self-sealing diaphragm for injection and/or extraction of reagents into the reaction vessel, and a seal mechanism comprising a movable plunger (7) arranged in the microwave exposure position and reversibly operable into abutting contact with an external side of the diaphragm where the plunger is effective for preventing an outward deflection of the diaphragm caused by an increase of internal pressure in the vessel.

The invention further suggests a method for confining a chemical reaction in a reaction vessel (1) that is accessible through a self-sealing diaphragm (5) covering an opening (4) of the reaction vessel. The method comprises the steps of injecting/extracting reagents through the self-sealing diaphragm, and applying a controllable counter pressure to an external side of the diaphragm that counteracts an outward deflection of the diaphragm caused by an increase of internal pressure in the vessel.

Advantageous embodiments are further specified in the following detailed disclosure.

SHORT DESCRIPTION OF THE DRAWINGS

The invention is more closely explained below with reference made to the diagrammatic drawings, wherein.

DETAILED DESCRIPTION OF THE INVENTION

Illustrating examples and preferred embodiments of the invention will be described in detail below with reference made to the drawings.

Figure 1:
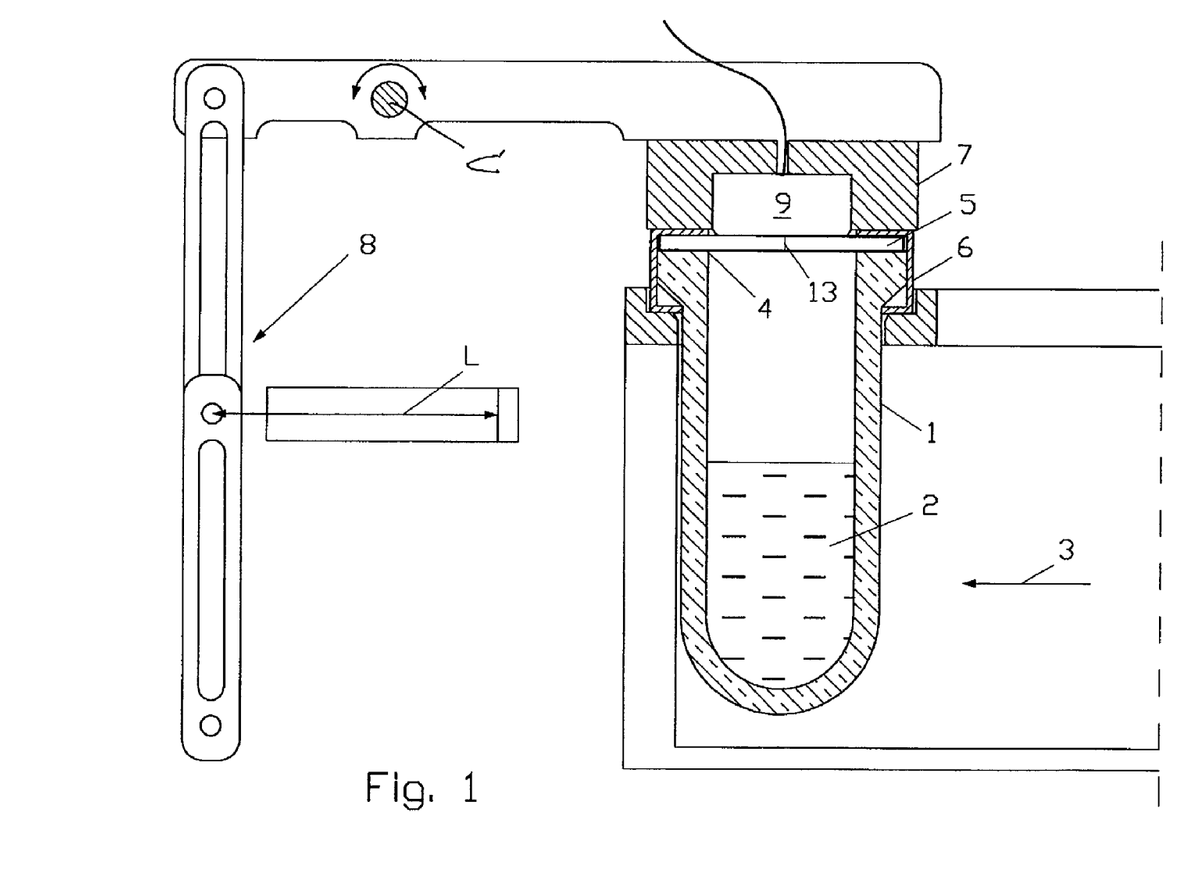
FIG. 1 is a partial view of an apparatus incorporating a seal mechanism for a reaction vessel according to the invention.

FIG. 1 shows a reaction vessel 1 containing the reacting mixture 2 that is exposed to microwaves 3, e.g. The reaction vessel 1 is a container typically made of glass, but can be formed in any material that withstands the temperatures and pressures that may be expected during a chemical reaction that takes place in the reaction vessel 1. The reaction vessel 1 may be formed as a vial, a test tube, or may have any other design suitable for a specific application. An opening 4 of the reaction vessel is covered by a lid or diaphragm 5 that is fastened to the reaction vessel by means of a cap 6, secured on an upper rim-portion or flange of the reaction vessel of FIG. 1.

In order to prevent a deflection outwards of the diaphragm 5 due to an increase of pressure caused by a chemical reaction in the reaction vessel or caused by a temperature rise of the substance in the vessel, a retaining plate or plunger 7 is brought into abutting contact with the diaphragm 5.

The plunger 7 of FIG. 1 is pivotally supported about an axis C and reversibly movable between a position where the diaphragm is accessible to be punctured for injection and/or extraction, respectively, and an operational position wherein the plunger is brought into abutting contact with the self-sealing diaphragm 5. The plunger 7 may alternatively be manually operated. The motion of the plunger 7 preferably is electrically, hydraulically or pneumatically driven. A drive means may be acting directly on the plunger via a rotating drive shaft (e.g., coincident with the axis C), or indirectly connected with the plunger via a mechanical arrangement 8 as illustrated in FIG. 1.

The plunger 7 basically is controlled to apply a constant external pressure to the diaphragm. Optionally, the plunger 7 carries a pressure gauge 9 for measuring the internal pressure acting on the diaphragm 5 and urging the diaphragm outwards. The pressure gauge 9 is advantageously connected to an apparatus for monitoring the pressure in the reaction vessel 1. Hazardous pressure levels may thus be detected and the process controlled with respect to safe process conditions. The detected internal pressure in the reaction vessel may alternatively be used for continuously controlling the plunger to apply a counter-pressure on the diaphragm that is related to the detected internal pressure in the reaction vessel.

Figure 2:
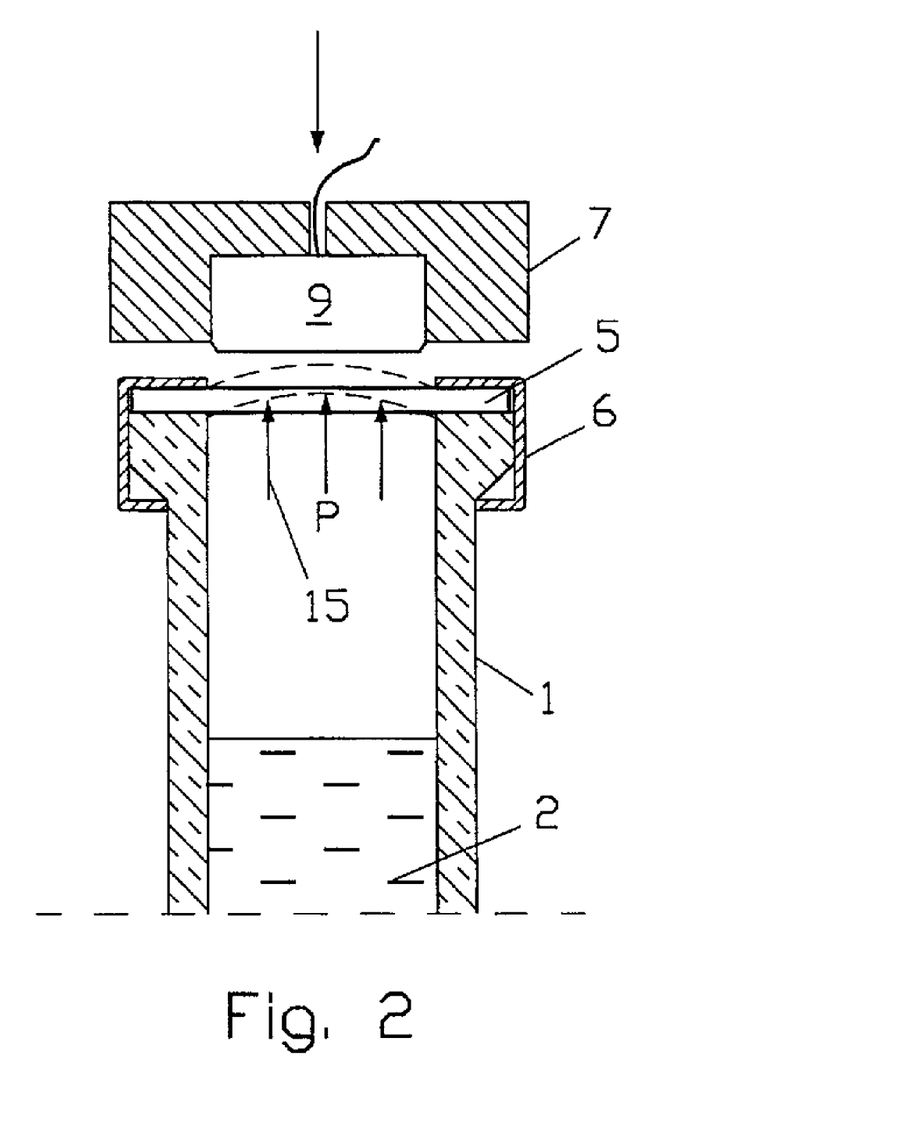
FIG. 2 is a partially sectioned view showing a reaction vessel and a plunger incorporated in the seal mechanism of the invention.

FIG. 2 shows a reaction vessel 1 and a plunger 7 comprising a pressure gauge 9. The diaphragm 5 is fastened to the reaction vessel by means of the cap 6, the cap being attached to the round going flange in the open end of the reaction vessel 1. A pressure (p) 15 is acting on the inner side of the diaphragm 5, urging the diaphragm towards the pressure gauge/plunger.

Figure 3:
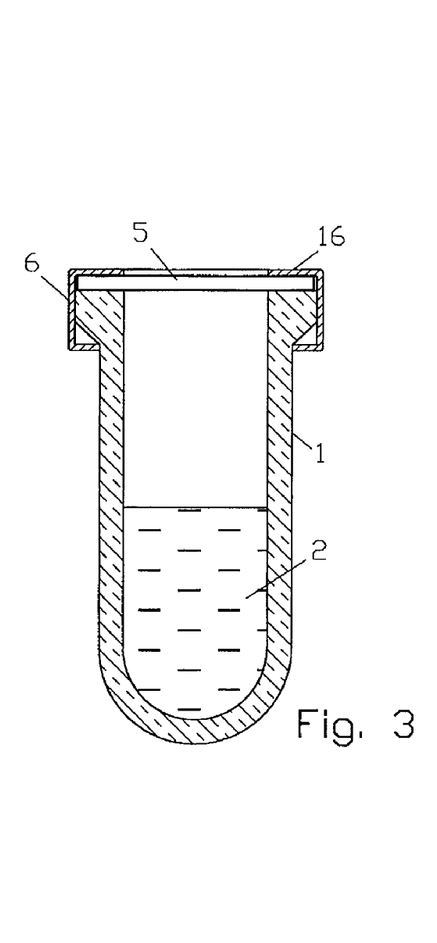
FIG. 3 is a sectional view showing a reaction vessel according to the invention.

FIG. 3 shows a reaction vessel 1 with reacting mixture 2 and a diaphragm 5 fastened to the reaction vessel by means of the cap 6.

Figure 4:
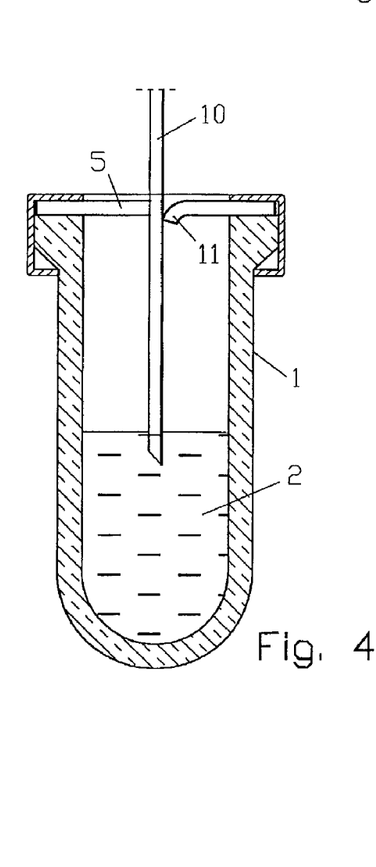
FIG. 4 shows the reaction vessel of FIG. 3 and a needle puncturing a penetrable diaphragm of the reaction vessel.

FIG. 4 shows a needle 10 penetrating the diaphragm 5, causing a slit or tab 11 to be formed in the diaphragm. The tab 11 is allowed to swing back and close the penetration when the needle is withdrawn through the diaphragm. Typically, a penetration does not cause any material to be removed from the diaphragm. As will be understood from the following disclosure, the invention provides a reliable seal of the vessel also if material is removed from the diaphragm as a result of repeated penetration by the needle 10 or similar dispensing means.

Figure 5:
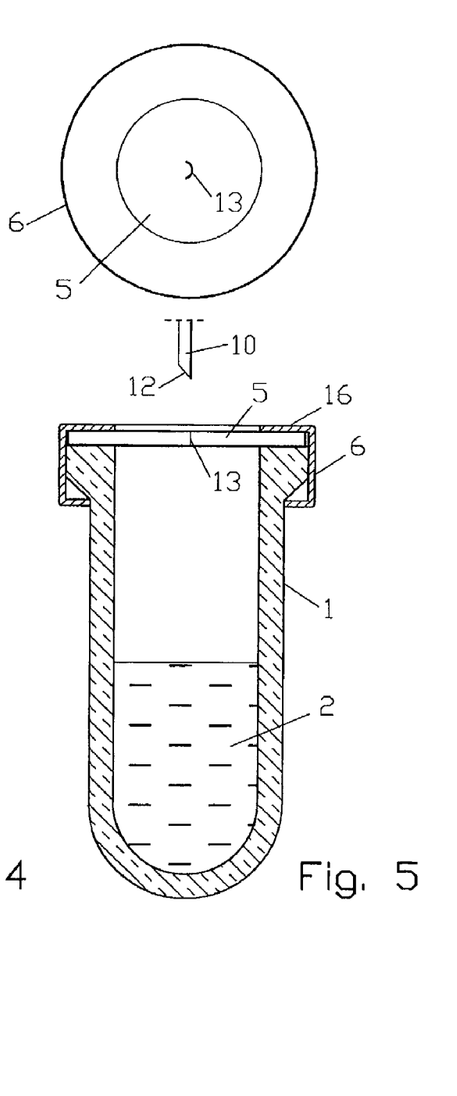
FIG. 5 shows the needle and reaction vessel after penetration.

FIG. 5 shows a needle 10 penetrating the diaphragm 5. The needle 10 has a chambered needlepoint 12 that provides inclined cutting surfaces in the diaphragm upon penetration. Further, the needlepoint has a rounded shape, when seen in cross-section, so that a curved penetration 13 is produced through the diaphragm.

Figure 6:
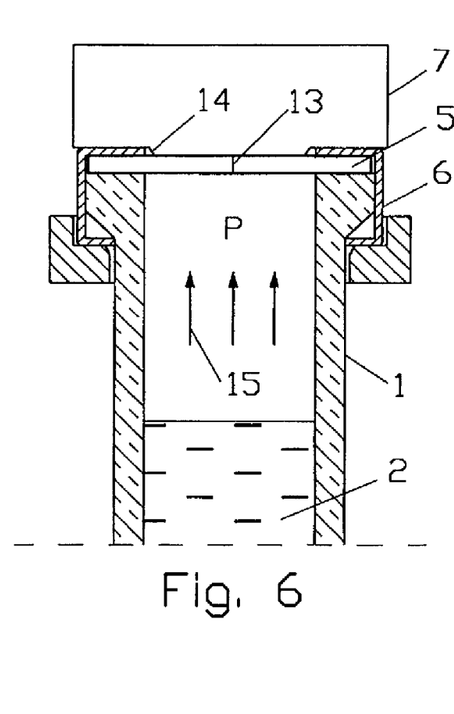
FIG. 6 is a partially sectioned view showing an alternative embodiment of the plunger and a reaction vessel.

FIG. 6 shows a reaction vessel 1 and a plunger 7 that has a protruded portion 14, which abuts the external side of the diaphragm 5 and thus keeps the penetration 13 closed.

Figure 7:
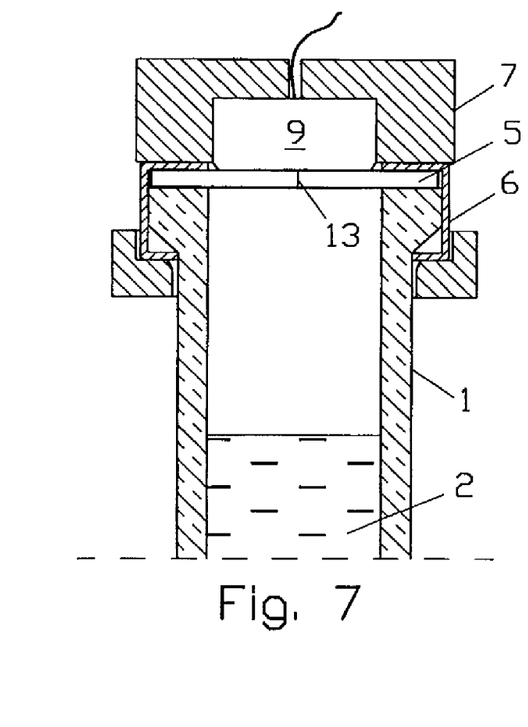
FIG. 7 is a partially sectioned view showing the plunger of FIG. 6 carrying a pressure detecting means.

FIG. 7 shows a reaction vessel 1 and a plunger 7, as shown in FIG. 6, and wherein the plunger carries a pressure gauge 9.

According to a first aspect of the invention there is suggested a seal mechanism for a penetrable, pressure proof sealing of a reaction vessel having an opening and a penetrable lid or diaphragm 5 covering at least said opening. The seal mechanism comprises a retaining plate or plunger 7 arranged to be pressed against at least a part of an external side of said diaphragm opposite to said opening, so as to provide a pressure proof sealing of the reaction vessel also when the diaphragm has been penetrated.

Advantageously, the reaction vessel 1 is a vial or a test tube, but it can be any type of container serving as a reaction vessel and having an opening 4 through which a substance may be injected to and/or extracted from the inner volume of the vessel. The diaphragm covers the opening, said opening being defined by an annular end surface of the straight cylindrical wall of the tubular vessel. In a preferred embodiment, the vessel opening is defined by a radial, protruding collar or flange formation, running around the open end of the reaction vessel, and the diaphragm covers the opening so that a peripheral portion of the diaphragm abuts said flange of the reaction vessel.

The diaphragm may be glued or welded to the flange portion. In the preferred embodiment, the reaction vessel further comprises a cap 6 for fastening said diaphragm to the reaction vessel. Advantageously, the cap may have an axial cylindrical portion that is crimped about the flange so that a ring-shaped end wall 16 of the cap covers at least a peripherally outer portion of the diaphragm 5. Alternatively, the cap and reaction vessel may be in threaded engagement. The cap may be formed in any suitable material, such as metal, plastics, etc.

Preferably, the diaphragm is made of elastic or elastomer material, such as rubber, synthetic rubber or other synthetic material having self-sealing properties. As used herein, the expression "self-sealing" should be understood as referring to a material that heals after puncture and therefore allows repeated penetration for injecting e.g. a reagent or solvent to a substance in the reaction vessel, or for extracting an amount of the content there from. A suitable material is characterized by intrinsic elastic properties and a capacity for contraction and closing a slit through the diaphragm that is made by a needle or similar penetration means. The material is chosen for imperviousness and chemical resistance with respect to the reacting substances in the vessel.

Penetration is made by a needle or other dispensing means with a capacity for penetrating the diaphragm. In the following disclosure, a penetrating needle is used for illustration purposes though it will be apparent for a man skilled in the art, that the inventive solution is applicable to any other combination of penetrable diaphragm and penetrating dispensing means. A needle may be formed with a chambered point so as to provide an inclined cut through the diaphragm and in such way that no material is removed/cut out from the diaphragm, when the needle penetrates it. The penetration causes a slit or tab 11 to be formed in the material. When the needle is withdrawn through the diaphragm, the tab swings back and closes the penetration by means of the meeting, inclined cutting surfaces. When an increase of internal pressure generated from the chemical reaction in the reaction vessel, the tab will close the diaphragm from inside the reaction vessel. The plunger is then operable to provide a counter support that prevents an outward deflection of the diaphragm that would separate the meeting cutting surfaces of the penetration, and thus prevents a leakage or evaporation through the penetration.

The plunger 7 is typically formed from non-elastic materials such as metal, plastic, composite materials, etc. The plunger is operable into abutting contact with the external side of the diaphragm and may be controlled to initially contact the diaphragm without applying any substantial external pressure thereto. The plunger may be controlled to exert a constant pressure to the diaphragm. When the pressure inside the reaction vessel increases as a result of the chemical reaction that takes place in the reaction vessel, the plunger may alternatively be controlled to apply a balancing external pressure to the diaphragm that counteracts an outward deflection of the diaphragm.

Basically, the plunger is reversibly movable between an operational position where it is pressed or held against the external side of the diaphragm, and a retracted position where it is removed from the diaphragm so that the reaction vessel is accessible for injection and/or extraction, respectively, through the diaphragm. The plunger may be controlled for linear motion in axial direction of the reaction vessel. The motion of the plunger may alternatively involve a generally axial component and a generally radial component relative to the vessel, e.g., such that the plunger is first lifted and then laterally displaced from the vessel opening.

Preferably though, the plunger is pivotally driven about an axis C between the operational and retracted positions, respectively. The means for pivoting the plunger may be manually, electrically, hydraulically or pneumatically driven. For example, the rotary shaft of an electric motor may be arranged to pivot the plunger about the axis C and directly or indirectly connected with the plunger or the axis C. Preferably, a linear drive unit L is arranged to pivot the plunger about the axis C via a mechanical link system as illustrated in FIG. 1. The linear drive unit L advantageously is realized as a pneumatic or hydraulic cylinder unit.

In order to prevent an unexpectedly high internal pressure in the reaction vessel from dislocating the plunger in its operational position, the seal mechanism may further comprise locking means (not shown in the drawings) for securing the plunger in the operational position.

Typically, the reaction vessel is utilized for chemical reactions where an increase in temperature and pressure is expected. The pressure inside the reaction vessel may amount to the order of about 10–20 bar and the internal temperature may amount to the order of about 60°–250° C., for example. However, the claimed invention is not limited to specific pressure and temperature ranges, and the seal mechanism and plunger may be dimensioned to operate at pressures above 100 bar and with temperatures above 250° C.

For provoking or accelerating a chemical reaction between two or more substances in the reaction vessel, an increase in the temperature may be required. In order to heat the substances, any conventional heating method is applicable. Typically, the reaction vessel is exposed to microwave energy. The reaction vessel is then positioned such that at least the part of the reaction vessel holding the substances is exposed to microwaves.

For monitoring the pressure inside the reaction vessel, the plunger may comprise a pressure gauge for measuring the internal pressure acting on the diaphragm. Thus, it is possible to avoid hazardous overpressure inside the reaction vessel by controlling the plunger to operate as a safety switch that releases pressure to prevent the vessel from cracking, or by controlling the process to stay below safe pressure levels. In another aspect, a continuous monitoring of the internal pressure provides the possibility also for dimensioning the pressure that the plunger applies to the external side of the diaphragm in relation to the internal pressure.

The plunger may be dimensioned for contacting at least the part of the diaphragm covering the opening in the reaction vessel, and the plunger may additionally contact the annular portion of the cap that covers the peripheral area of the diaphragm. Alternatively, the plunger may be dimensioned to press/act exclusively on an area of the diaphragm comprising the penetration/penetrations made by the needle or other penetration means.

According to a second aspect the invention relates to an apparatus for performing chemical reactions, wherein a plurality of reaction vessels are supported and successively moved, in parallel or in series, to a position for microwave energy exposure. The apparatus comprises dispensing means capable of penetrating a self-sealing diaphragm of the reaction vessels for injection and/or extraction of reagents into the reaction vessel where a chemical reaction takes place, and a seal mechanism as disclosed above arranged in the microwave exposure position for confining the chemical reaction in the reaction vessel.

Said dispensing means preferably comprises the needle disclosed above, and control mechanics associated with the needle for vertically driving the needle through the diaphragm in a dispensing/extraction position of the reaction vessel. Alternatively, the needle is operable for penetration of the diaphragm when the reaction vessel is located in the heating position. In another embodiment, the needle is movable and controlled for penetration of the diaphragm of a reaction vessel that is located in another position in the apparatus, separated from the heating position. Reagents, buffer solutions and wash liquids, as appropriate, are accommodated in the apparatus and accessible for the needle or other dispensing means.

The apparatus further comprises a shielded microwave generator, mechanical guides and drive means for the needle and for moving each reaction vessel, individually or in sets, to and from the microwave exposure position. Control logic and operator interface for monitoring and evaluation of the chemical reactions performed by the apparatus are preferably integrated in an automated system wherein the apparatus is incorporated. The structural layout of the apparatus is not further specified herein, and may be adapted to user specifications and contemplated reactions or assays to be carried out by the apparatus.

According to a third aspect, the invention relates to a method for confining a chemical reaction in a reaction vessel 1 that is accessible through a self-sealing diaphragm 5 covering an opening 4 of the reaction vessel. The method comprises the steps of injecting/extracting reagents through the self-sealing diaphragm, and applying a controllable counter pressure to an external side of the diaphragm that counteracts an outward deflection of the diaphragm caused by a rising internal pressure in the reaction vessel.

Preferably, a plunger is pivotally operable into abutting contact with the external side of the diaphragm from a retracted position wherein the diaphragm is accessible, such as for penetration by a needle. The plunger typically is activated towards the operational position while exposing the reagents in the reaction vessel to heat, such as microwave energy.

In the best mode of employment, the counteracting pressure applied to the diaphragm is advantageously dimensioned in relation to the internal pressure generated by the chemical reaction in the reaction vessel, continuously detected by a pressure detecting means supported on the plunger that is operable for supplying the external pressure on the diaphragm.

Modifications of structural details in the general solution suggested above are incorporated within the scope of the claims attached hereto.

The invention claimed is:

1. A seal mechanism for confining a chemical reaction in a reaction vessel having an inner volume that is accessible through a penetrable, self-sealing diaphragm covering an opening of the reaction vessel and through which reagents are at least one of injected and extracted, wherein the inside of the vessel is accessible through a portion of the self-sealing diaphragm; said seal mechanism comprising
 a movable plunger cooperating with said self-sealing diaphragm, said plunger being reversibly operable between a retracted position wherein the inner volume of the reaction vessel is accessible through the diaphragm, and an operational position in abutting contact with the diaphragm, wherein
 the plunger is effective to counteract an outward deflection of the diaphragm caused by an increase of internal pressure in the vessel, and in the operational position, the movable plunger is in abutting contact with the portion of the diaphragm through which the inner volume of the reaction vessel is accessible.

2. The seal mechanism of claim 1, wherein the plunger is pivotally movable about an axis (C).

3. The seal mechanism of claim 2, wherein the drive unit controls the pivoting motions and applied pressure of the plunger via a link mechanism.

4. The seal mechanism of claim 1, wherein the plunger is driven for a linear motion in axial direction of the vessel.

5. The seal mechanism of claim 1, wherein the plunger is driven in a motion having a generality axial component and a generally radial component with respect to the axial direction of the vessel.

6. An apparatus for performing chemical reactions, comprising: one or more reaction vessels supported and successively movable to a position for microwave energy exposure, each reaction vessel having a penetrable, self sealing diaphragm covering an opening of the reaction vessel, wherein the inside of the vessel is accessible through a portion of the self-sealing diaphragm;
 a dispenser capable of penetrating the self-sealing diaphragm for at least one of injection and extraction of reagents into the reaction vessel where the chemical reaction takes place; and
 a movable plunger cooperating with said one or more reaction vessels in the microwave exposure position, the plunger being reversibly operable between a retracted position wherein an inner volume of the vessel is accessible through the diaphragm, and an operational position in abutting contact with the self sealing diaphragm, wherein
 the plunger is effective to counteract an outward deflection of the diaphragm caused by an increase of internal pressure in the vessel and in the operational position, the movable plunger is in abutting contact with the portion of the diaphragm through which the inner volume of the reaction vessel is accessible.

7. The apparatus of claim 6, wherein the plunger is pivotally supported to be pivoted about an axis (C).

8. The apparatus of claim 7, wherein the plunger is associated with the driver by which the plunger is pivoted via link mechanism.

9. The apparatus of claim 8, wherein a pressure monitor is connected with the plunger.

10. The apparatus of claim 9, wherein the pressure monitor continuously dimensions the external pressure applied by the plunger relative to the detected internal pressure in the reaction vessel.

11. The apparatus of claim 7, wherein a pressure detector is supported on the plunger.

12. A seal mechanism for confining a chemical reaction in a reaction vessel having an inner volume that is accessible through a penetrable, self-sealing diaphragm covering an opening of the reaction vessel and through which reagents are at least one of injected and extracted; said seal mechanism comprising
 a movable plunger cooperating with said self-sealing diaphragm, said plunger being reversibly operable between a retracted position wherein the inner volume of the reaction vessel is accessible through the diaphragm, and an operational position in abutting contact with the diaphragm, wherein
 the plunger is effective to counteract an outward deflection of the diaphragm caused by an increase of internal pressure in the vessel, and
 a linear drive unit controls pivoting motions and applied pressure of the plunger via a link mechanism.

13. An apparatus for performing chemical reactions, comprising:
 one or more reaction vessels supported and successively movable to a position for microwave energy exposure, each reaction vessel having a penetrable, self sealing diaphragm covering an opening of the reaction vessel;

a dispenser capable of penetrating the self-sealing diaphragm for at least one of injection and extraction of reagents into the reaction vessel where the chemical reaction takes place; and a movable plunger cooperating with said one or more reaction vessels in the microwave exposure position, the plunger being reversibly operable between a retracted position wherein an inner volume of the vessel is accessible through the diaphragm, and an operational position in abutting contact with the self sealing diaphragm, wherein the plunger is effective to counteract an outward deflection of the diaphragm caused by an increase of internal pressure in the vessel, and the plunger is associated with a linear driver by which the plunger is pivoted via a link mechanism.

* * * * *